United States Patent
Lima et al.

(10) Patent No.: US 9,308,370 B2
(45) Date of Patent: Apr. 12, 2016

(54) STIMULATION OF A HYPOGLOSSAL NERVE FOR CONTROLLING THE POSITION OF A PATIENT'S TONGUE

(71) Applicant: ImThera Medical, Inc., San Diego, CA (US)

(72) Inventors: Marcelo G. Lima, San Diego, CA (US); Paul M. Meadows, Glendale, CA (US); Jasper Benke, San Diego, CA (US)

(73) Assignee: IMTHERA MEDICAL, INC., San Diego, CA (US)

( * ) Notice: Subject to any disclaimer, the term of this patent is extended or adjusted under 35 U.S.C. 154(b) by 0 days.

(21) Appl. No.: 14/400,733

(22) PCT Filed: May 13, 2013

(86) PCT No.: PCT/US2013/040728
§ 371 (c)(1),
(2) Date: Nov. 12, 2014

(87) PCT Pub. No.: WO2013/173214
PCT Pub. Date: Nov. 21, 2013

(65) Prior Publication Data
US 2015/0148860 A1 May 28, 2015

Related U.S. Application Data

(60) Provisional application No. 61/647,122, filed on May 15, 2012.

(51) Int. Cl.
*A61N 1/00* (2006.01)
*A61N 1/36* (2006.01)
*A61N 1/05* (2006.01)

(52) U.S. Cl.
CPC .......... *A61N 1/3611* (2013.01); *A61N 1/36167* (2013.01); *A61N 1/0551* (2013.01); *A61N 1/0556* (2013.01)

(58) Field of Classification Search
CPC ............. A61B 5/4818; A61N 1/36003; A61N 1/36014; A61N 1/0548; A61N 1/37229
See application file for complete search history.

(56) References Cited

U.S. PATENT DOCUMENTS

| | | | |
|---|---|---|---|
| 7,809,442 B2 | 10/2010 | Bolea et al. | |
| 2005/0085874 A1* | 4/2005 | Davis | A61N 1/37205 607/66 |
| 2010/0094379 A1 | 4/2010 | Meadows et al. | |
| 2011/0112601 A1 | 5/2011 | Meadows et al. | |
| 2014/0379049 A1* | 12/2014 | Mashiach | A61N 1/37229 607/60 |

* cited by examiner

*Primary Examiner* — Robert N Wieland
(74) *Attorney, Agent, or Firm* — Morgan, Lewis & Bockius LLP

(57) ABSTRACT

A method for controlling a position of a patient's tongue includes attaching at least one electrode to the patient's hypoglossal nerve, applying an electric signal through the electrode to the hypoglossal nerve to stimulate at least one muscle of the tongue at least until the number of obstructive sleep apnea occurrences are reduced from an initial level to a treatment level, and reducing the application of the electric signal while the number of obstructive sleep apnea occurrences remain generally at or below the treatment level.

16 Claims, 8 Drawing Sheets

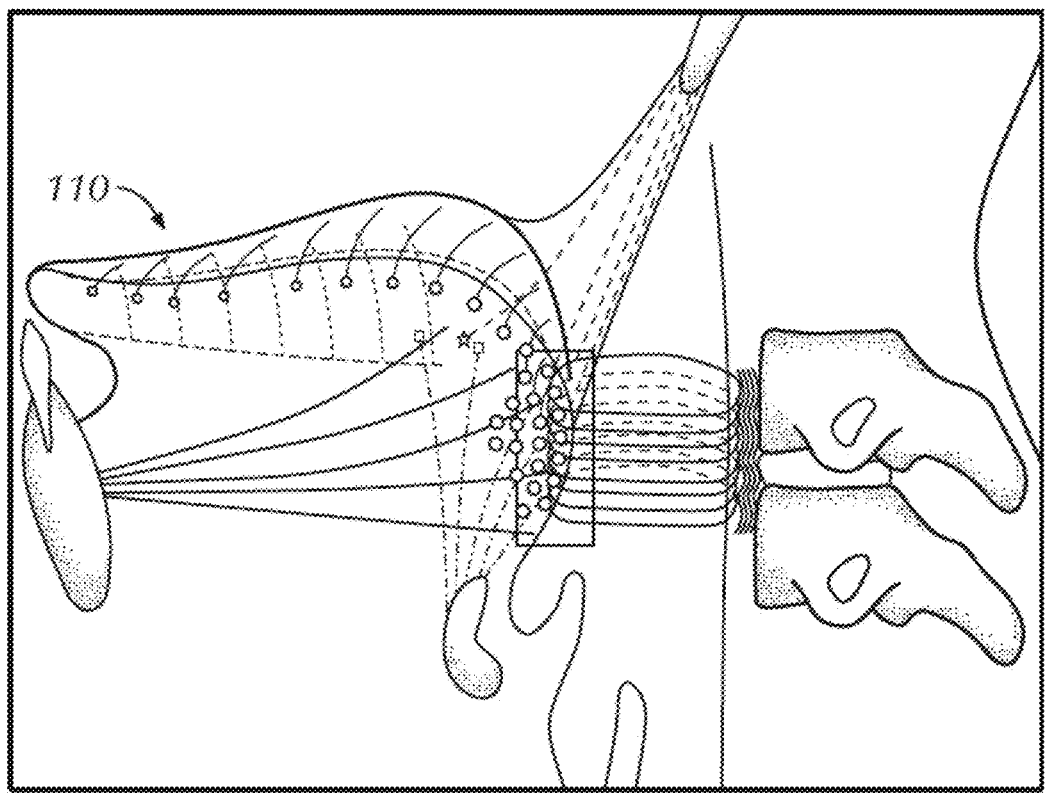
FIG. 1
*(Prior Art)*
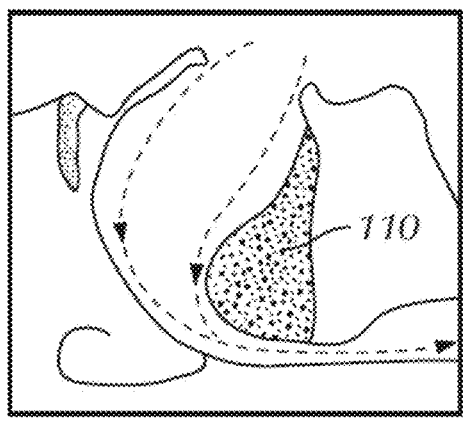 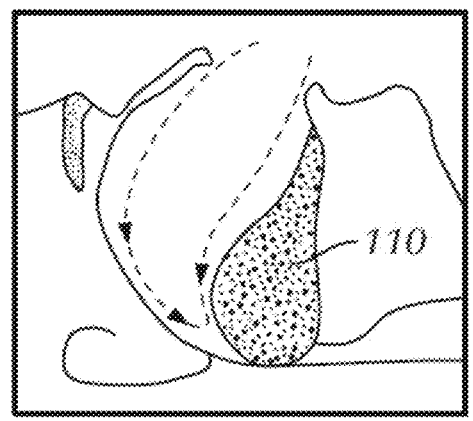
FIG. 2A
*(Prior Art)*
FIG. 2B
*(Prior Art)*

| Paramet er | Diagno stic | 3 Months | p-value (D vs 3) | 12 months | p-value (D vs 12) | Stim OFF | p-value (D vs Off) | p-value (12 vs Off) |
|---|---|---|---|---|---|---|---|---|
| AHI | 42.6 ± 13.8 | 13.6 ± 11.9 | <0.007 | 15.4 ± 4.8 | <0.002 | 14.4 ± 8.0 | <0.007 | 0.749 |
| 4% ODI | 22.9 ± 12.4 | 7.9 ± 6.2 | <0.025 | 8.3 ± 5.8 | <0.012 | 7.9 ± 5.4 | <0.035 | 1 |
| MAI | 34.3 ± 7.7 | 17.4 ± 4.9 | <0.004 | 20.6 ± 6.3 | <0.002 | 22.3 ± 4.3 | <0.006 | 0.421 |

Fig. 10

STIMULATION OF A HYPOGLOSSAL NERVE FOR CONTROLLING THE POSITION OF A PATIENT'S TONGUE

CROSS-REFERENCE TO RELATED APPLICATIONS

This application is a National Stage Patent Application of International Application No. PCT/US2013/040728, filed May 13, 2013, which claims the benefit of U.S. Provisional Patent Application No. 61/647,122 filed May 15, 2012 entitled "Stimulation of a Hypoglossal Nerve for Controlling the Position of a Patient's Tongue", each of which is incorporated by reference herein in its entirety.

BACKGROUND OF THE INVENTION

The present invention generally relates to stimulation of a hypoglossal nerve for controlling the position of a patient's tongue. In one embodiment, the hypoglossal nerve is stimulated to prevent obstructive sleep apnea.

Sleep apnea is a sleep disorder characterized by pauses in breathing during sleep. Those affected by sleep apnea stop breathing during sleep numerous times during the night. There are two types of sleep apnea, central and obstructive sleep apnea. Central sleep apnea is a failure of the nervous system to produce proper signals for excitation of the muscles involved with respiration. Obstructive sleep apnea ("OSA") is caused by episodes of physical obstruction of the upper airway channel ("UAW") during sleep. Referring to FIGS. 1, 2A and 2B, the physical obstruction is often caused by changes in the position of the tongue 110 during sleep that results in the closure of the soft tissues at the rear of the throat or pharynx.

OSA is characterized by the obstruction of the airway causing breathing to cease completely (Apnea) or partially (Hypopnea). The human airway (at the level of the thorax) is lined by soft tissue, any collapse of its walls results in the closure of the airway which leads to insufficient oxygen intake, thereby interrupting one's sleep (episodes or micro-arousals).

During sleep, the tongue muscles relax. In this relaxed state, the tongue may lack sufficient muscle tone to prevent the tongue from changing its normal tonic shape and position. When the base of the tongue and soft tissue of the upper airway collapse, the upper airway channel may become blocked, causing an apnea event (see FIG. 2B). Blockage of the upper airway prevents air from flowing into the lungs, creating a decrease in blood oxygen level, which in turn increases blood pressure and heart dilation. This causes a reflexive forced opening of the upper airway channel until normal patency is regained, followed by normal respiration until the next apneaic event. These reflexive forced openings briefly arouse the patient from sleep.

The severity of OSA is determined by dividing the number of episodes of apneas and hypopneas lasting ten seconds or more by the number of hours of sleep. The resulting number is called the Apnea-Hypopnea Index, or AHI. The higher the index the more serious the condition. An index between 5 and 10 is low, between 10 and 15 is mild to moderate, over 15 is moderately severe, and anything over 30 indicates severe sleep apnea. Other indices may also be used to classify the severity of OSA. Oxygen Desaturation Index ("ODI") for example, is calculated by dividing the total number of oxygen desaturations (4% decrease in $SaO_2$ (at nadir) with an increase to within 1% of the prehypopnea baseline value) by the number of hours of sleep. Micro Arousal Index ("MAI") is defined as the total number of short duration arousals divided by the number of hours of sleep.

Current treatment options for OSA range from drug intervention, non-invasive approaches, to more invasive surgical procedures. A standard method for treating OSA is Continuous Positive Airway Pressure ("CPAP") treatment, which requires the patient to wear a mask through which air is blown into the nostrils and mouth to keep the airway open.

OSA treatments are intended to be used by the patient every sleep session. Withdrawal of known treatments results in the immediate return of OSA within the first night of off treatment (see "Effects of Continuous Positive Airway Pressure Therapy Withdrawal in Patients with Obstructive Sleep Apnea" by Kohler et al.). FIG. 3 illustrates the data from ambulatory pulse-oximetry and CPAP machine download showing the mean (+/−SE) nightly apnea-hypopnea index (AHI) (top graph) and oxygen desaturation index (ODI) (bottom graph) of patients withdrawn from CPAP (Placebo-CPAP, solid circles) and of patients continuing CPAP (open circles).

There is therefore a need for an improved treatment for OSA.

BRIEF SUMMARY OF THE INVENTION

In one embodiment there is a method for controlling a position of a patient's tongue including attaching at least one electrode to the patient's hypoglossal nerve; applying an electric signal through the electrode to the hypoglossal nerve to stimulate at least one muscle of the tongue at least until the number of obstructive sleep apnea occurrences are reduced from an initial level to a treatment level; and reducing the application of the electric signal while the number of obstructive sleep apnea occurrences remain generally at or below the treatment level. In one embodiment, reducing the application of the electric signal includes applying the electric signal having an Intra-Session Periodicity. In one embodiment, reducing the application of the electric signal includes applying the electric signal having an Inter-Session Periodicity.

In one embodiment, reducing the application of the electric signal includes reducing a duration that the electric signal is applied. In one embodiment, reducing the application of the electric signal includes ceasing application of the electric signal. In one embodiment, reducing the application of the electric signal includes reducing a frequency that the electric signal is applied. In one embodiment, reducing the application of the electric signal includes reducing an amplitude that the electric signal is applied.

In a further embodiment, the method further comprises applying an initial electric signal that gradually increases and then levels off. In one embodiment, the electric signal is applied to at least one targeted motor efferent of the hypoglossal nerve. In one embodiment, the electric signal is applied when the patient is asleep. In one embodiment, the electric signal is applied when the patient is awake.

In another embodiment, there is a method for controlling a position of a patient's tongue includes attaching at least one electrode to the patient's hypoglossal nerve; applying an electric signal through the electrode to the hypoglossal nerve at an Inter-Session Periodicity to stimulate at least one muscle of the tongue to reduce the number of obstructive sleep apnea occurrences.

In another embodiment, there is a method for controlling a position of a patient's tongue includes attaching at least one electrode to the patient's hypoglossal nerve; applying an electric signal through the electrode to the hypoglossal nerve at an Intra-Session Periodicity to stimulate at least one muscle of the tongue to reduce the number of obstructive sleep apnea occurrences.

In another embodiment, there is a system for controlling a position of a patient's tongue that includes at least one electrode configured to attach to the patient's hypoglossal nerve; and an implantable pulse generator programmed to perform any of the methods disclosed herein.

In another embodiment, there is a computer readable storage medium having stored thereon computer-executable instructions which, when executed by a processor, perform a any of the methods disclosed herein.

BRIEF DESCRIPTION OF THE SEVERAL VIEWS OF THE DRAWINGS

The foregoing summary, as well as the following detailed description of exemplary embodiments of a system and method for stimulating a hypoglossal nerve for controlling a position of a patient's tongue, will be better understood when read in conjunction with the appended drawings. It should be understood, however, that the invention is not limited to the precise arrangements and instrumentalities shown.

In the drawings:

FIG. 1 is an illustration of the human airway;

FIG. 2A is an illustration of an open human airway;

FIG. 2B is an illustration of a closed human airway during an apnea event;

FIG. 10 is a chart from the residual study including data used to generate FIGS. 7-9.

DETAILED DESCRIPTION OF THE INVENTION

Figure 3:
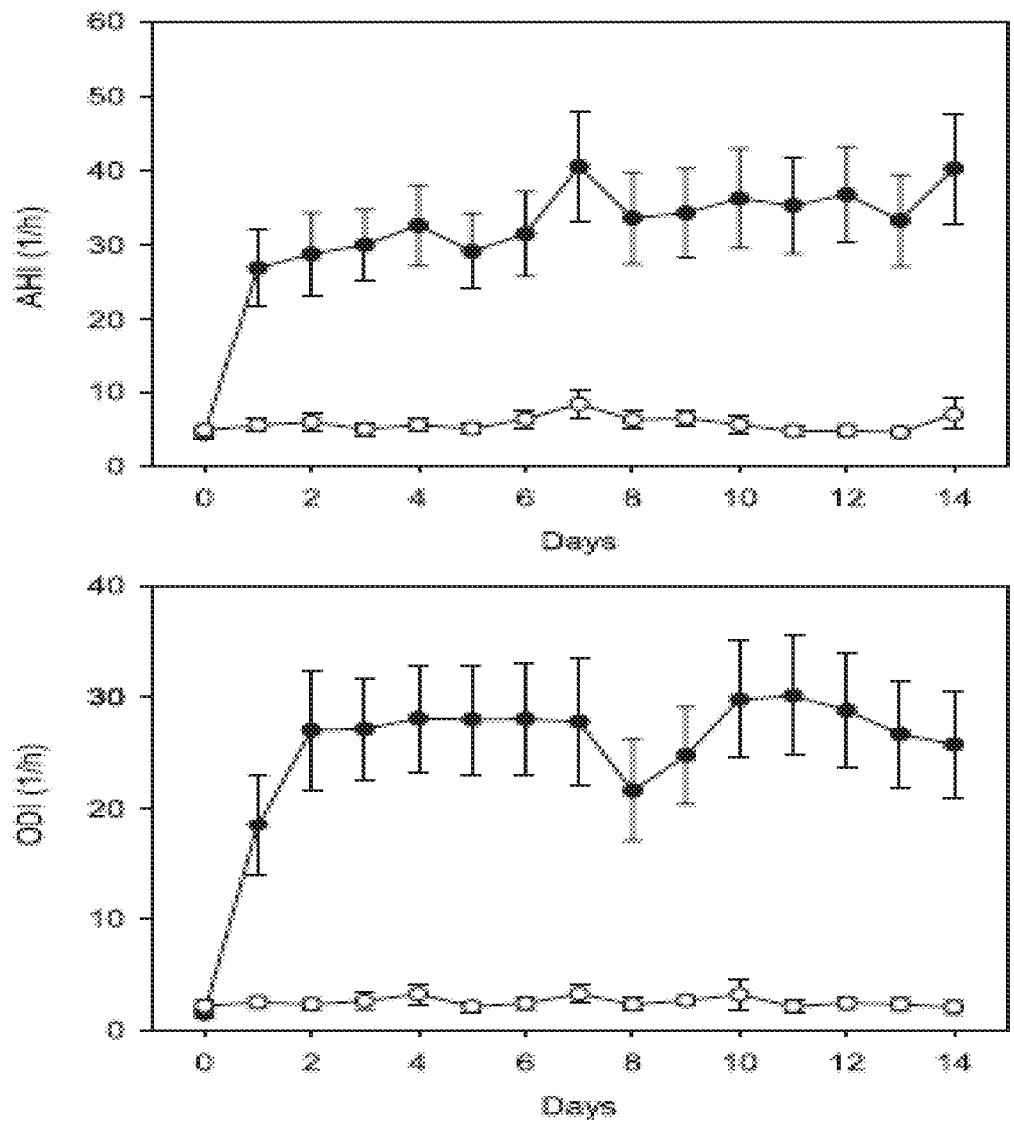
FIG. 3 is a graphical illustration of data from ambulatory pulse-oximetry and CPAP machine download.

In some embodiments, the systems and methods disclosed herein provide not only a treatment for obstructive sleep apnea ("OSA"), but also a disease modifying therapy. In some embodiments, stimulation of the hypoglossal nerve ("HGN") exerts a residual beneficial effect even after the stimulation is temporarily discontinued and/or reduced.

In one embodiment, after attaching at least one electrode to the patient's hypoglossal nerve an electric signal is applied through the electrode to the hypoglossal nerve to stimulate at least one muscle of the tongue at least until the number of obstructive sleep apnea occurrences are reduced from an initial level to a treatment level and then the application of the electric signal is reduced while the number of obstructive sleep apnea occurrences remain generally at or below the treatment level.

As used herein, "Intra-Session Periodicity or Intermittency" means the reduced or temporary ceased stimulation within a single sleep session and "Inter-Session Perodicity or Intermittency" means the reduced or temporary ceased stimulation of sleep sessions as a whole. Reduction of stimulation may include reducing the level (e.g., frequency or amplitude) of the stimulation from a treatment level.

Though the patient may elect to receive therapy when they are awake, the electrical signals are applied when the patient is sleeping, either during the day or at night. The system may be preprogrammed to deliver the treatment schedules to the patient. In one embodiment, the patient can input into the system (e.g., using a remote control or bed side monitor) when they are about to go to sleep and the stimulation program begins after a predetermined time (e.g., 30 minutes) to allow the patient to fall asleep. The system may be programmed to turn off at a predetermined time or when the patient turns the system Off when they get up for the day. In alternative embodiments, the system is turned On and Off based on movement of the patient such as the patient's proximity to a bedside device (e.g. they sit up or walk closer to the bedside device).

After a first stimulation treatment schedule or therapy session (e.g., 3 months of nightly use), the application of the electric signal may be reduced to a second stimulation treatment schedule or therapy session while the efficacy of the treatment achieved during the first stimulation treatment schedule is at least generally retained during the second stimulation treatment schedule.

Reducing the level and/or schedule of stimulation after a period of time, while the treatment level of OSA occurrences is at least generally retained, may lengthen the life of the implanted device (e.g., doubling or tripling the life of the implant) due to reduced use of the implant which in turn lowers surgical risks to patients. Reducing the stimulation while maintaining efficacy of treatment may also increase comfort (e.g., the patient is less likely to be awakened by the device) and ease of compliance (e.g., the patient may not need to have the device turned On every night).

Figure 4:
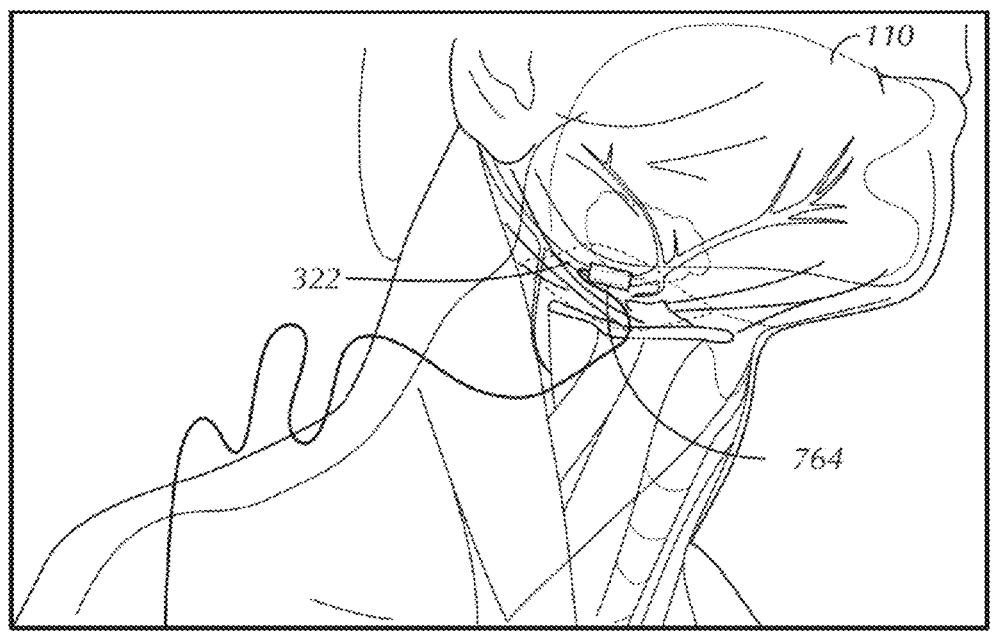
FIG. 4 is an exemplary illustration of an electrode attached to a patient's hypoglossal nerve.
Figure 5:
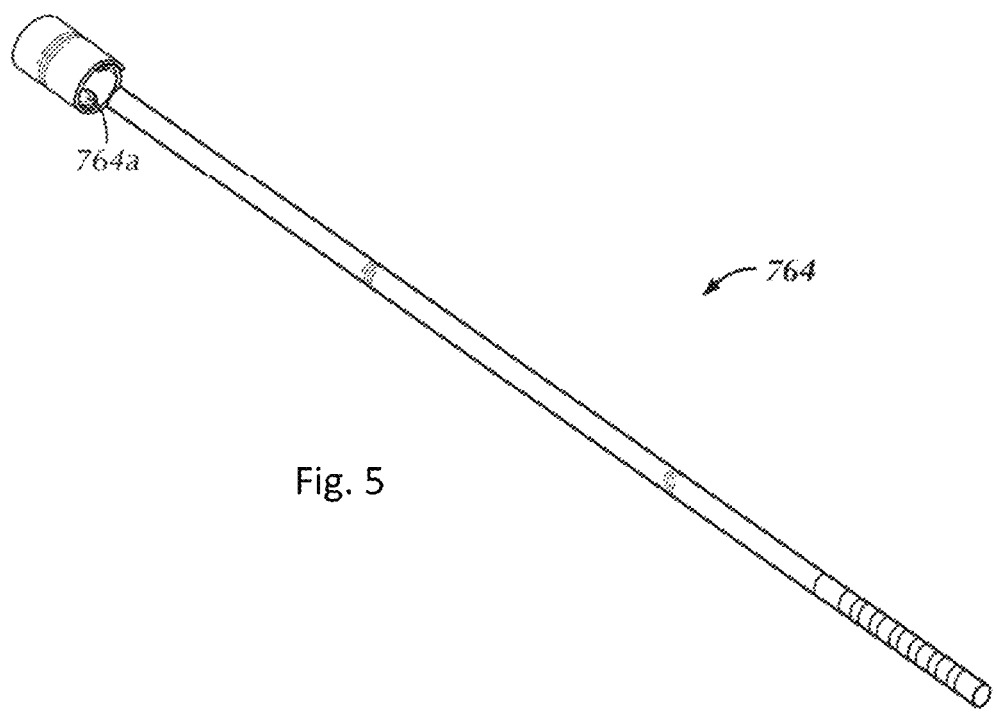
FIG. 5 is a perspective view of the electrode.
Figure 6:
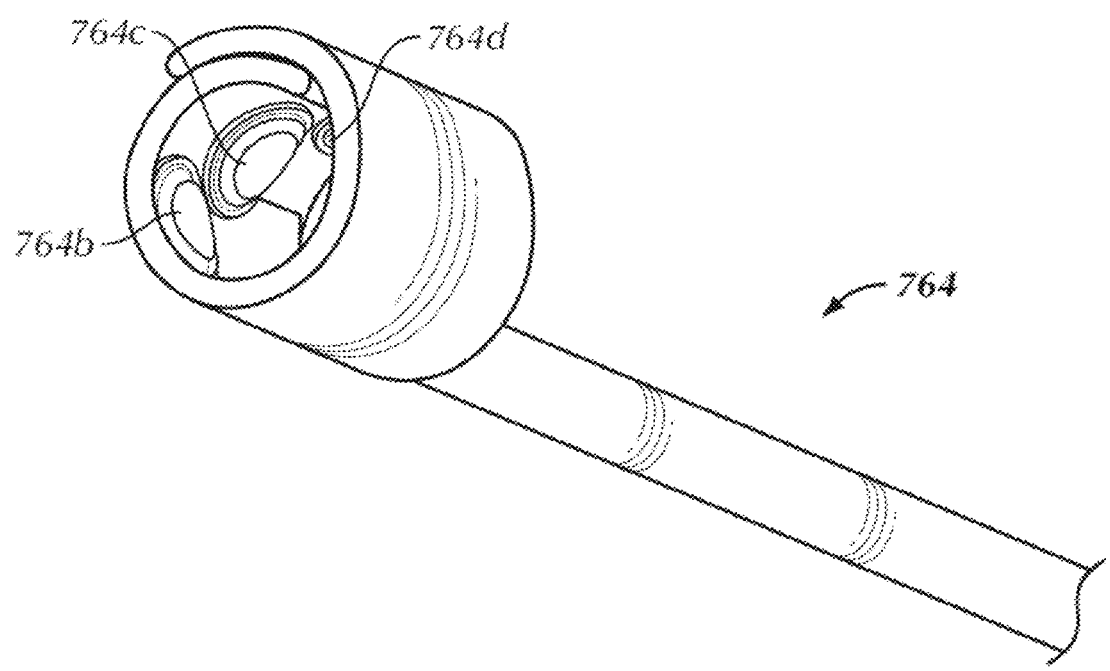
FIG. 6 is a perspective view of the electrode showing the plurality of contacts.
Figure 7:
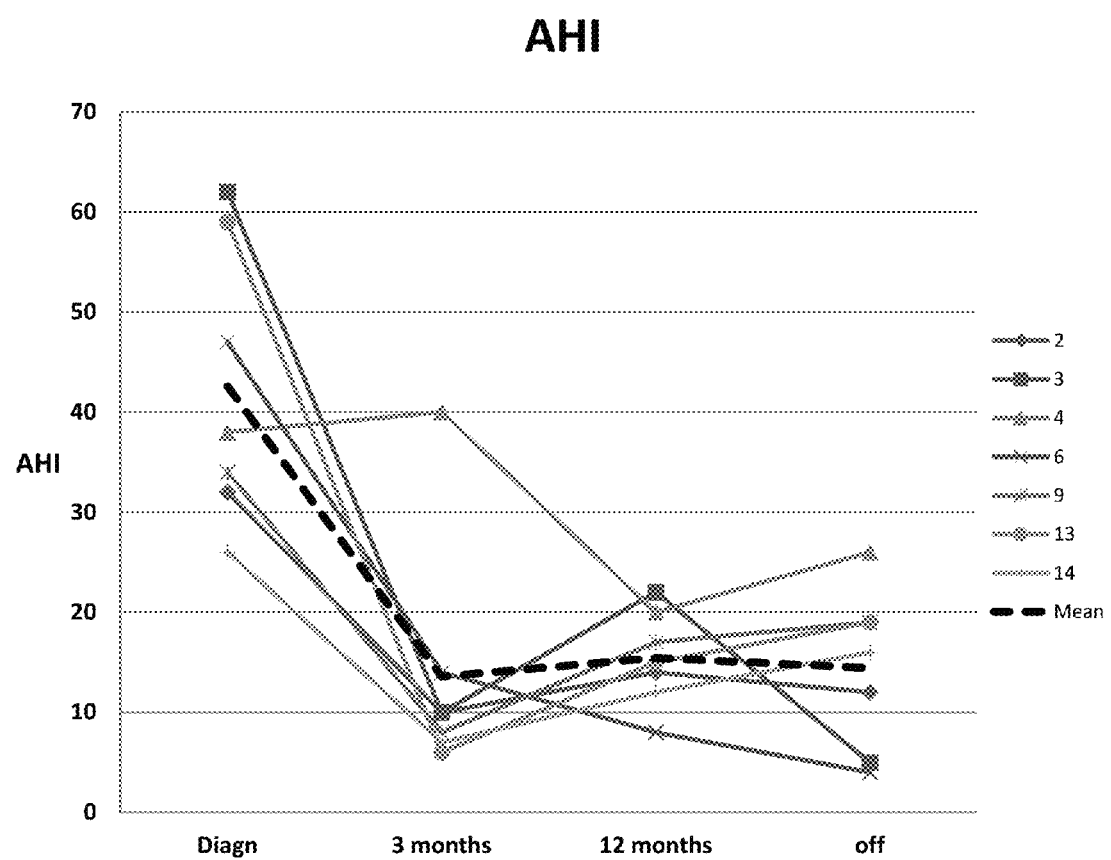
FIG. 7 is a graphical representation of the individual and mean results from a study of Apnea-Hypopnea Index ("AHI") over 12 plus months.
Figure 8:
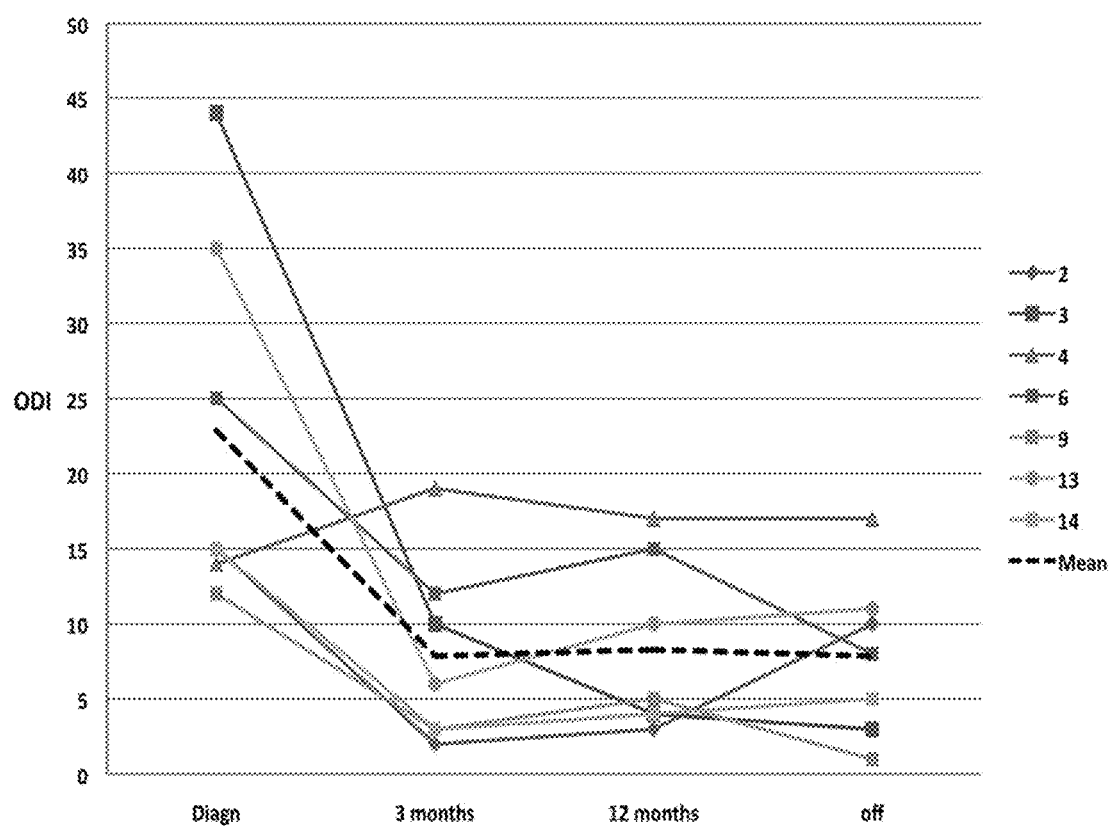
FIG. 8 is a graphical representation of the individual and mean results from a study of Oxygen Desaturation Index ("ODI") over 12 plus months.
Figure 9:
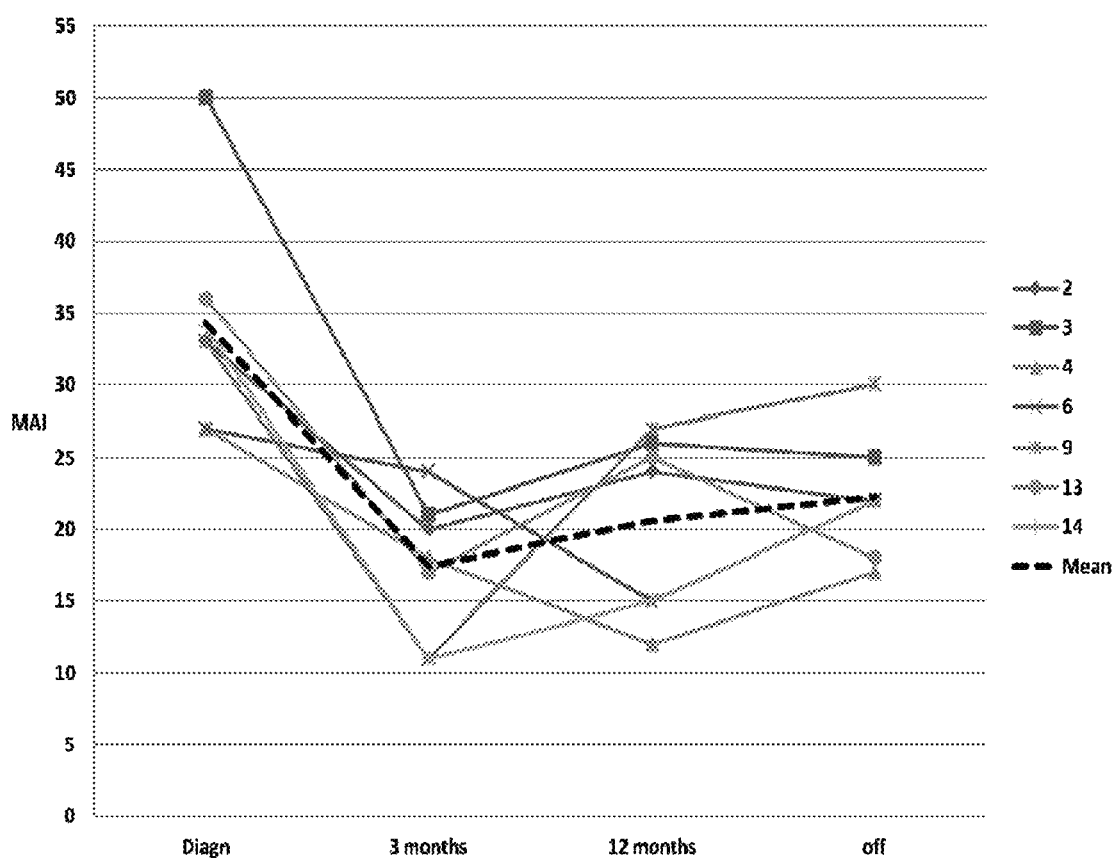
FIG. 9 is a graphical representation of the individual and mean results from a study of Micro Arousal Index ("MAI") over 12 plus months.

Referring to FIGS. 4 and 5, in one exemplary embodiment, an electrode 764 is implanted around the hypoglossal nerve 322 at or near an approximately 1 cm length of 2.5 to 4.5 mm diameter nerve bundles. This is typically at the rear of and below the mandible, just underneath the sub-mandibular gland, proximal to the Styloglossus/Hyoglossus branches and distal to the ansa cervicalis branch. At this point, the major branches to the various tongue muscles are distal to the electrode site. The systems described in U.S. Patent Application Publication Nos. 2010/0094379 and 2011/0112601, which are hereby incorporated by reference in their entirety, may be adapted for use with the systems and methods disclosed herein.

In one embodiment, the present invention is directed to a method of treating, controlling, or preventing a neurological disorder by attaching at least one programmable electrode 764a, 764b, 764c, 764d to a patient's hypoglossal nerve proper 322; and periodically applying electric signals to motor efferents located within the hypoglossal nerve proper 322 through the programmable electrode 764 to selectively stimulate at least one muscle. In one embodiment, the electric signals are modulating. In one embodiment, the method of treating, controlling, or preventing a neurological disorder consists essentially of the recruitment of retrusor motor efferents. In one embodiment, the method comprises the recruitment of protrusor motor efferents. In one embodiment, the method comprises the recruitment of a ratio of retrusor to protrusor motor efferents such as the ratios described above to treat a neurological disorder.

The neurological disorder suitable for treatment, control, or prevention by the present invention is selected from the group consisting of, but not limited to oral myofunctional disorders, atrophies, weakness, tremors, fasciculations, and myositis. In one embodiment, the neurological disorder is obstructive sleep apnea. Other potential applications of this method, in addition to treatment of obstructive sleep apnea, include, for example, supplemental nerve stimulation to keep the airway open for treatment of snoring, hypopnea, or countering motor activation of the tongue during a seizure. Other health problems related to the patency of a patient's airway may also be treated using methods provided by the present invention.

Specific hypoglossal nerve efferents may be selectively stimulated by one or more electric signals. The electric signals may be emitted from at least one programmable electrode contact. In one embodiment, the targeted selective stimulation of hypoglossal nerve efferents occurs via two or more electrode contacts. In one embodiment, the targeted selective stimulation of hypoglossal nerve efferents is driven by multiple current sources. In one embodiment, the multiple electrode contacts are each driven by their own independent current source.

In one embodiment, the method includes activating the ipsilateral Geniohyoid muscle. In one embodiment, the method includes activating rostral or caudal or both compartments of the ipsilateral Geniohyoid muscle. In one embodiment, the method includes activating at least one compartment or both compartments of ipsilateral or with the rostral compartment of the contralateral Geniohyoid muscles increasing the dilation (of the pharyngeal airway) and the patency of the airway channel.

In one embodiment, the targeted selective stimulation of hypoglossal nerve efferents activates at least one lingual muscle. In one embodiment, the targeted selective stimulation of hypoglossal nerve efferents activates at least one upper airway channel dilator muscle. In one embodiment, at least one protrusor muscle is activated. In one embodiment, at least one protrusor muscle and at least one retrusor muscle are alternately activated. In one embodiment, at least one protrusor muscle and at least one retrusor muscle are co-activated. In one embodiment, the at least one protrusor muscle activated is the genioglossus muscle. In one embodiment, at least one beneficial muscle group is activated. In one embodiment, at least two beneficial muscle groups are activated.

The modulating electric signals may have a frequency sufficient for a smooth tetanic contraction. In one embodiment, the modulating electric signals have a stimulation frequency, at least during the treatment schedule, of about 10 to about 40 pps. The modulating electric signals may be of an intensity, at least during the treatment schedule, from about 10 to about 3000 microamps ($\mu A$). In one embodiment, the modulating electric signals have a stimulation pulse width, at least during the treatment schedule, of about 10 to about 1000 microseconds ($\mu s$).

After attaching at least one electrode to the patient's hypoglossal nerve, an electric signal may be applied through the electrode to the hypoglossal nerve to stimulate at least one muscle of the tongue. The electric signal may be applied at least until the number of obstructive sleep apnea occurrences are reduced from an initial level to a treatment level. In one embodiment, the application of the electric signal is reduced while the number of obstructive sleep apnea occurrences is generally retained at or below the treatment level.

An acceptable level of obstructive sleep apnea occurrences may be determined and a treatment schedule and/or level of stimulation may be determined to maintain this level. In one embodiment, an Apnea-Hypopnea Index, an Oxygen Desaturation Index and/or a Micro Arousal Index of the patient as a result of the treatment is less than approximately 50% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 45% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 40% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 35% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 30% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 25% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 20% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 15% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 10% of the Apnea-Hypopnea Index, an Oxygen Desaturation Index and/or a Micro Arousal Index prior to treatment. In one embodiment, an Apnea-Hypopnea Index, an Oxygen Desaturation Index and/or a Micro Arousal Index of the patient as a result of the treatment is less than approximately 5% of the Apnea-Hypopnea Index, an Oxygen Desaturation Index and/or a Micro Arousal Index prior to treatment.

In one embodiment, the duration that the electric signal is applied is reduced after an initial treatment period while the number of obstructive sleep apnea occurrences is retained generally at or below a treatment level. In one embodiment, the frequency that the electric signal is applied is reduced after an initial treatment while the number of obstructive sleep apnea occurrences remain generally at or below the treatment level. In one embodiment, the amplitude that the electric signal is applied is reduced after an initial treatment while the number of obstructive sleep apnea occurrences remain generally at or below the treatment level.

The initial treatment period may be considered to be periodic (e.g., the system is On while the patient is sleeping and turned Off when the patient is awake). The reduced treatment schedule may be less frequent than the initial treatment schedule (e.g., therapy is not delivered every night). The initial treatment period may be any desired period (e.g., from 1 month to 12 months in duration) and thereafter intermittent treatment ensues. In one embodiment, the initial treatment period is more than 1 year. In one embodiment, the initial treatment period is more than 11 months. In one embodiment, the initial treatment period is more than 10 months. In one embodiment, the initial treatment period is more than 9 months. In one embodiment, the initial treatment period is more than 8 months. In one embodiment, the initial treatment period is more than 7 months. In one embodiment, the initial treatment period is more than 6 months. In one embodiment, the initial treatment period is more than 5 months. In one embodiment, the initial treatment period is more than 4 months. In one embodiment, the initial treatment period is more than 3 months. In one embodiment, the initial treatment period is more than 2 months. In one embodiment, the initial treatment period is more than 1 month. In one embodiment, the initial treatment period is more than 1 week. In one embodiment, the initial treatment period is less than 1 week.

After an initial treatment period, the electric signal may no longer be applied for a period of time but the number of obstructive sleep apnea occurrences may remain generally at or below the treatment level. In one embodiment, the electric signal is not applied for 24 hours or longer after an initial treatment while the number of obstructive sleep apnea occurrences remain generally at or below the treatment level. In one embodiment, the electric signal is not applied for 48 hours or longer after an initial treatment while the number of obstructive sleep apnea occurrences remain generally at or below the treatment level. In one embodiment, the electric signal is not applied for 72 hours or longer after an initial treatment while the number of obstructive sleep apnea occurrences remain generally at or below the treatment level. In one embodiment, the electric signal is not applied for 1 month or longer after an initial treatment while the number of obstructive sleep apnea occurrences remain generally at or below the treatment level. In one embodiment, the electric signal is not applied for 6 months or longer after an initial treatment while the number of obstructive sleep apnea occurrences remain generally at or below the treatment level.

In one embodiment, the electric signal is reapplied after a period of not applying the electric signal. In one embodiment, the electric signal is applied at a first predetermined treatment schedule and then a second predetermined treatment schedule. The patient may be reevaluated after one or more treatment schedules to determine the minimum stimulation required to maintain the number of obstructive sleep apnea occurrence generally at the treatment level. After determining the minimum stimulation required, the system may then be reprogrammed. Alternatively, the system may be initially programmed to automatically switch from the first treatment schedule to the second treatment schedule after a predetermined amount of time (e.g., after 12 months). The second treatment schedule may be reduced in the number of consecutive sessions (e.g., from delivering one or more electrical signals every night to delivering one or more electrical signals only on weeknights) and/or reducing the frequency, duration, and/or amplitude of the electrical signal during each sleep session.

A first treatment schedule may be followed by one or more reduced treatment schedules. In one embodiment, a first treatment schedule includes applying electric signals every night and a second treatment schedule includes not applying an electric signal for one or more nights. In one embodiment, the treatment schedule may be further reduced from the initial schedule such that the reduction is a gradual decrease (e.g., from 360 consecutive nights of applying an electrical signal to 20 consecutive nights of applying an electrical signal to 10 consecutive nights of applying an electrical signal to 5 consecutive nights of applying an electrical signal to a schedule of applying an electrical signal every other night to a schedule of applying an electrical signal every third night). In one embodiment, a second treatment schedule may include reducing the number of hours an electric signal is applied each night. In one embodiment, a second treatment schedule may include pausing the electric signal one or more times each night. In one embodiment, a second treatment schedule may include increasing the delay before therapy begins after the system is turned On.

If the number of obstructive sleep apnea occurrences increases after reducing the amount of electrical signals, then the system may be reprogrammed to increase the level and/or amount of electrical signals until the number of obstructive sleep apnea occurrences are below a certain level. In one embodiment, the patient can select or at least partially schedule the reduced treatment schedule. For example, during the reduced treatment schedule the patient may be permitted two nights a week to forgo stimulation. The patient may input predetermined nights in which no therapy will be delivered (e.g., Friday and Saturday nights) or a monitor can indicate if a night could be skipped (e.g., the system was used for 6 consecutive nights so a light or message my indicate that the patient can skip a night). In one embodiment, the patient can program nights they would rather not have therapy delivered and the system will set a treatment schedule (e.g., if the patient plans on being on vacation for three days at the end of the month, the system may change the treatment schedule to deliver therapy every night leading up to the vacation to help prevent OSA occurrences from happening during the vacation).

The schedule of delivering electrical signals may be automatically adjusted to account for a missed night that was not part of the scheduled program. For example, if a scheduled Off night is programmed for Wednesday but the patient travels on Tuesday without bringing the external elements described below such that no signal is applied that night, the system may shift the program ahead one night so that Tuesday is treated as the scheduled Off night and the electrical signals are applied on Wednesday.

Periodic monitoring of the patient may be used to determine the appropriate stimulation level needed to keep the number of obstructive sleep apnea occurrences at the treatment level. If the patient or doctor determines that the number of obstructive sleep apnea occurrences increases after reducing the amount of electrical signals, then the system may be reprogrammed to increase the level and/or amount of electrical signals until the number of obstructive sleep apnea occurrences are below a certain level.

The patient may elect to apply the electric signal while he or she is awake in order to exercise or train his or her tongue to stay out of his or her airway in addition to or in place of the stimulation schedules discussed above. For example, if the level of electrical stimulation needed to reduce the obstructive sleep apnea occurrences causes the patient to wake up, the patient may chose to have a desired amount of electrical stimulation applied to his or her HGN while he or she is awake in place of or to supplement the stimulation applied to his or her HGN while he or she is asleep. In one embodiment, the patient may elect to have the electrical stimulation applied for an hour right before he or she goes to sleep such that no stimulation is needed while he or she sleeps or at least the level of electrical stimulation required while he or she sleeps can be reduced and the number of obstructive sleep apnea occurrences remain below a desired level.

In one embodiment, the patient initiates all sleep sessions through a remote control. In one embodiment, the patient may voluntarily control when and how often therapy is applied, or the therapy could be initiated by the patient every night but the controller could implement the agreed upon schedule, or the system could be programmed using a real time clock to implement the therapy at pre-determined times and at pre-determined schedules.

Exemplary methods of Inter-Session Perodicity or Intermittency may include:

Example 1: pre-defined days of operation (On Monday, Wednesday and Friday; Off Thursday, Friday, Saturday and Sunday), biweekly schedules, etc.;

Example 2: randomized days of operation; and

Example 3: randomized session use not tied to a day.

Exemplary methods of Intra-Session Periodicity or Intermittency may include:

Example 1: a device having 6 contacts, each cycle includes turning each contact On then Off once where the timing is staggered and the use is overlapped (contact 1 is turned on for 5 seconds at time 0, contact 2 is turned on for 5 seconds at 4 seconds in, contact 3 is turned on for 5 seconds at 9 seconds in, etc), stimulation is on for 3 cycles, off for the duration that 2 cycles would occupy, then this repeats;

Example 2: on for 3 cycles, off for 4 cycles, on for 2 cycles, off for one cycle (stochastic or randomized periodicity);

Example 3: randomization only applied to cycles that are on (on for 3 cycles, off for 2 cycles, on for 2 cycles, off for 2 cycles, on for 5 cycles, off for 2 cycles . . . ); and Example 4: randomization only applied to cycles that are off (on for 3 cycles, off for 2 cycles, on for 3 cycles, off for 5 cycles, on for 3 cycles, off for 4 cycles . . . ).

An exemplary progression of treatment for a patient includes:

Phase 1—The patient gets use to sensation of stimulation by starting stimulation at low levels, gradually increase the stimulation over time (e.g., days, weeks, etc.) to therapeutically useful levels that the patient tolerates without causing the patient to wake from painful or irritating levels of stimulation;

Phase 2—The patient uses therapy at a consistent level that provides airway clearance and trains the muscle and brain in the "proper" tongue activity; and Phase 3—the therapy levels are reduced (by any method above) thereby extending the useful lifetime of the implant and unnecessary stimulation while still promoting and maintaining "proper" tongue activity because, for example, the tongue muscles are more fit or the brain is re-trained.

Exemplary Study

A 12-month clinical study of unilateral Targeted Hypoglossal Neurostimulation (THN) was performed in 13 patients using the system and method as described above, including a multi-contact cuff electrode positioned around the proximal trunk of the hypoglossal nerve, targeting and stimulating selected contacts cyclically during both inspiration and expiration and inducing appropriate beneficial pharyngeal and oral tongue displacements.

In instances where the remote control and charger device used to start a sleep session malfunctioned (software or hardware) after receiving therapy for a period of time, patients did not feel the reappearance of OSA symptoms until the third or fourth night, sometimes even further. This happened multiple times during the course of the 12-month study to multiple patients.

Of the 13 subjects participating in and completing the 12-month THN feasibility study, 10 subjects (responders) had clinically meaningful results, reducing the intensity of the disease from severe to moderate or mild forms. Seven (7) of these subjects volunteered for consecutive night PSGs. On one of the nights (randomly determined) the stimulation was turned Off, whereas it was active on the other night. No significant negative residual side effects have been observed in these subjects over the 12-month course of the study, such as: swallowing difficulty; speech compromise; saliva choking; gaping; or muscular spasms.

Referring to FIGS. 7-10, "Off" refers to the night without stimulation. Patients 2, 3 and 9 were off stimulation on the first night. Patients 4, 6, 13 and 14 on the second night. There was no significant difference between the nights with and without stimulation after 12 months therapy. The nights without therapy after 1 year of therapy differed from the diagnostic nights as much as the nights with therapy after 1 year of therapy. After one year of nightly compliant use of THN, a significant statistical and clinical improvement was obtained in patients with moderate to mostly severe OSA, unable to use or comply with CPAP.

Withdrawal of THN for one night after the initial therapy did not reduce the accumulated improvements in the symptoms of OSA. The improvement obtained during THN remained unchanged for the Apnea-Hypopnea, the 4% Desaturation and the Micro-arousal Indices.

After a year of cyclical tonic stimulation (inspiratory & expiratory phases) for seven plus hours a night, the muscle fibers type and the fat content of the tongue may have changed. Alternatively or additionally, the hypoglossal nucleus may have modified firing properties of the HGN, perhaps mediated by the feedback loops via the afferent fibers (4 to 5%) of the HGN and/or other associated nerves. Finally, a new neural pathway in the HGN, established by the THN therapy, may have favorably influenced the coordination between extrinsic and intrinsic muscles in the tongue Hydrostat.

These findings demonstrate that reducing the stimulation therapy after an initial stimulation therapy may be an effective treatment of OSA e.g., by turning the stimulation "OFF" in intervals of one or two nights following an initial treatment and still get the full benefit of the treatment as if continuing to use it every night.

"On" or "Off" in the embodiments above may include total cessation of stimulation or a reduction in stimulation.

In one exemplary embodiment, the OSA system is comprised of implanted and external elements which together act to provide stimulation of the HGN 322. The implanted elements (the elements implanted into the patient) may include an implantable pulse generator ("IPG") and a cuff electrode 764. The external elements may include a remote control and charger ("RCC"), a charger coil and cable ("CC"), a docking station and a power supply for the patient, and a notebook computer and the aura clinical manager ("aCM") clinician's software programming system. The IPG may be responsible for generating the pulses that activate the desired neurons within the HGN 322, and is implanted in the anterior chest region of the patient. The cuff electrode 764 may attach to the IPG via an inline connector, and runs from the chest location of the IPG to the sub-mandibular region where it is wrapped around the HGN 322. The IPG may contain a plurality, such as six, independent current sources, each capacitively coupled via feedthroughs in its enclosure to the inline connector. The inline connector may have six torroidal spring contacts that mate with ring contacts of the cuff electrode 764 proximal connector. Each ring contact of the cuff electrode 764 may be connected by a wire in the cuff electrode 764 assembly to a contact within the self-sizing cuff. Each contact may be shaped to match the curvature of the nerve bundle of the HGN 322, and the six contacts are located within the cuff so that six sectors of the nerve circumference are in intimate contact with the cuff contacts. The IPG may be directed by the RCC to start and stop a sleep therapy treatment session, to provide information on the status of the IPG and the cuff electrode 764, and is used in conjunction with the CC to replenish the energy within the IPG battery. The aCM may be used by a clinical engineer or clinician to program the OSA system for use in providing therapy to the patient.

The system may include one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method for controlling a position of a patient's tongue, the method comprising:
   attaching at least one electrode to the patient's hypoglossal nerve;
   applying an electric signal through the at least one electrode to the hypoglossal nerve to stimulate at least one muscle of the tongue at least until a number of obstructive sleep apnea occurrences is reduced from an initial level to a treatment level; and
   reducing the application of the electric signal by a predetermined amount while the number of obstructive sleep apnea occurrences remains generally at or below the treatment level.

2. The method of claim 1, wherein reducing the application of the electric signal includes applying the electric signal having an Intra-Session Periodicity.

3. The method of claim 1, wherein reducing the application of the electric signal includes applying the electric signal having an Inter-Session Periodicity.

4. The method of claim 1, wherein reducing the application of the electric signal includes reducing a duration that the electric signal is applied.

5. The method of claim 1, wherein reducing the application of the electric signal includes ceasing application of the electric signal.

6. The method of claim 1, wherein reducing the application of the electric signal includes reducing a frequency that the electric signal is applied.

7. The method of claim 1, wherein reducing the application of the electric signal includes reducing an amplitude that the electric signal is applied.

8. The method of claim 1 further comprises:
   applying an initial electric signal that gradually increases over time and then levels off.

9. The method of claim 1, wherein the electric signal is applied to at least one targeted motor efferent of the hypoglossal nerve.

10. The method of claim 1, wherein the electric signal is applied when the patient is asleep.

11. The method of claim 1, wherein the electric signal is applied when the patient is awake.

12. A method for controlling a position of a patient's tongue, the method comprising:
    attaching at least one electrode to the patient's hypoglossal nerve;
    applying an electric signal through the at least one electrode to the hypoglossal nerve at a predetermined Inter-Session Periodicity to stimulate at least one muscle of the tongue to reduce a number of obstructive sleep apnea occurrences.

13. A method for controlling a position of a patient's tongue, the method comprising:
    attaching at least one electrode to the patient's hypoglossal nerve;
    applying an electric signal through the at least one electrode to the hypoglossal nerve at a predetermined Intra-Session Periodicity to stimulate at least one muscle of the tongue to reduce a number of obstructive sleep apnea occurrences.

14. A system for controlling a position of a patient's tongue, the system comprising:
    at least one electrode configured to attach to the patient's hypoglossal nerve; and
    an implantable pulse generator programmed to perform a method according to claim 1.

15. A non-transitory computer readable storage medium having stored thereon computer-executable instructions which, when executed by a processor, performs a method according to claim 1.

16. The method of claim 1, wherein reducing the application of the electric signal is conducted independent of feedback from the patient.

* * * * *